United States Patent
Rodriguez Ponce et al.

(10) Patent No.: US 8,060,181 B2
(45) Date of Patent: Nov. 15, 2011

(54) RISK ASSESSMENT FOR PLANNED TRAJECTORIES

(75) Inventors: Maria Inmaculada Rodriguez Ponce, München (DE); Christoph Pedain, München (DE); Andreas Hartlep, Naring (DE)

(73) Assignee: Brainlab AG, Feldkirchen (DE)

( * ) Notice: Subject to any disclaimer, the term of this patent is extended or adjusted under 35 U.S.C. 154(b) by 1010 days.

(21) Appl. No.: 11/697,823

(22) Filed: Apr. 9, 2007

(65) Prior Publication Data

US 2007/0244387 A1 Oct. 18, 2007

Related U.S. Application Data

(60) Provisional application No. 60/746,182, filed on May 2, 2006.

(30) Foreign Application Priority Data

Apr. 7, 2006 (EP) .................................... 06007425

(51) Int. Cl.
*A61B 17/52* (2006.01)
*A61M 21/00* (2006.01)
*A61F 5/00* (2006.01)
(52) U.S. Cl. .................... 600/411; 600/427; 600/439
(58) Field of Classification Search .................. 600/407
See application file for complete search history.

(56) References Cited

U.S. PATENT DOCUMENTS

| 6,026,316 A | 2/2000 | Kucharczyk et al. |
| RE37,410 E | 10/2001 | Brem et al. |
| 6,463,315 B1 * | 10/2002 | Klingberg et al. ............ 600/410 |
| 2002/0082498 A1 * | 6/2002 | Wendt et al. .................. 600/411 |
| 2003/0114751 A1 | 6/2003 | Pedain et al. |
| 2003/0208116 A1 | 11/2003 | Liang et al. |
| 2004/0015070 A1 * | 1/2004 | Liang et al. .................. 600/407 |
| 2004/0111183 A1 * | 6/2004 | Sutherland et al. ........... 700/245 |
| 2005/0137499 A1 * | 6/2005 | Sheets et al. .................. 600/562 |
| 2006/0052689 A1 | 3/2006 | Scouten et al. |
| 2007/0156156 A1 * | 7/2007 | Badie ........................... 606/129 |

FOREIGN PATENT DOCUMENTS

| EP | 0 945 815 | 9/1999 |
| EP | 1 396 233 | 3/2004 |

* cited by examiner

*Primary Examiner* — Tse Chen
*Assistant Examiner* — Hien Nguyen
(74) *Attorney, Agent, or Firm* — Renner, Otto, Boisselle & Sklar, LLP

(57) ABSTRACT

A method for planning the placement of a device in a body includes analyzing information of at least part of the internal structure of the body of a patient to determine if at least one specific or critical region or structure lies within a region of interest, said region of interest within a predetermined distance of the planned trajectory of the device in the body. Then, a level of risk is assessed to the at least one specific or critical region or structure that is within the region of interest.

22 Claims, 4 Drawing Sheets

RISK ASSESSMENT FOR PLANNED TRAJECTORIES

RELATED APPLICATION DATA

This application claims priority of U.S. Provisional Application No. 60/746,182 filed on May 2, 2006, which is incorporated herein by reference in its entirety.

FIELD OF THE INVENTION

The present invention relates to device and method for preparing and planning the placement of devices, such as, for example, biopsy needles, stimulators, probes or catheters, including intra-cranial catheters, in a body. More particularly, the invention relates to carrying out an infusion, drainage of a substance, such as fluid, into or out of tissue, or biopsies, preferably after having prepared and planned the placement of the device.

BACKGROUND OF THE INVENTION

In general, the term "infusion" is understood as any administration of a liquid or solid substance and/or an infusing medium, such as pharmaceutical substances, cells, genes, enzymes, proteins, liposomes, antibodies, hormones, viral vectors, viruses or the like. The substance may be introduced directly into a body and/or into body tissues, for example, in order to reach a pre-defined target area and/or to bypass the effect of the blood-brain barrier. The substance can be delivered within a relatively short period of time, for example through an injection, or over a longer period of time, for example at a continuous and possibly variable rate of delivery of the substance.

Pharmaceutical substances previously have been administered by injecting a substance through the skin, directly into the vascular system, muscle tissue or subcutaneous tissue, or by positioning a catheter such that a substance could be introduced directly into the targeted body tissues. Administration depends on the experience of the person who positions the syringe or catheter so as to position or deliver the administered substance as precisely as possible in the desired area of tissue. Furthermore, the behavior of said substance in the specific area of tissue is known and taken into consideration to ensure that the resulting distribution of the substance matches the desired target area.

Due to intrinsic and unavoidable inaccuracies related to the planning and placement procedure (e.g., from image resolution registration inaccuracy, etc.), and to different levels of experience of the executing physician and/or the lack of knowledge of the patient-specific tissue configuration, as well as due to patient-specific variations in the arrangement of the tissue, for example in the case of a diseased tissue, it has been necessary to leave sufficient space between critical areas (in terms of a specific level of risk, automatically and/or manually defined) in order to ensure that the catheter does not interfere with the critical area. These areas include, for example, eloquent brain areas, vascular structures or anatomical areas such as ventricles or the optic nerve.

Another consideration is the actual trajectory of the catheter relative to the critical areas. Thus, although there might be a trajectory that avoids all non-desired areas and structures, this trajectory might not be chosen if it is in close proximity to critical areas. Therefore, to avoid the risk of injuring a critical area, the catheter is not placed as close as possible to an area to be treated.

On the other hand, when performing an infusion, it is preferable that the substance distribution resulting from the infusion optimally matches the desired target area. In the case of suboptimal catheter placement, this may necessitate that a larger amount of a toxic treatment substance is infused than would have been necessary if the catheter was placed in close proximity or directly into the area to be treated.

According to the prior art, trajectories for biopsies or intra-cranial catheters are planned prior to neurosurgery. The planning is based on target selection and on a selection of the entry point of the trajectory. To perform a minimally invasive surgical procedure, the physician plans the trajectory in consideration of critical brain areas. These areas might consist of critical and anatomical structures, such as ventricles, or physiological, vascular or functional structures.

Various methods and devices have already been proposed for enabling a substance to be introduced into a particular area of tissue, or for developing more efficient treatments that can be used to treat, for example, tumors, Parkinson's disease or other diseases.

It is known from U.S. RE 37,410 E to inject a substance to be administered into a biodegradable material and to arrange the latter within or closely adjacent to a tumor to be treated, in order for example to bypass the effect of the blood-brain barrier in the case of a brain tumor. Once the bio-degradable material has degraded, the substance contained therein is released. This delivery method based on diffusive processes, however, is relatively imprecise with respect to individual, patient-specific dosage.

U.S. Pat. No. 6,026,316 describes a method for delivering medicines using data obtained from magnetic resonance imaging (MRI) to determine the position of the delivery device and to monitor the spatial distribution of the delivered medicine.

US-2003-01-147051-A1 discloses a method for planning an infusion, wherein patient data is captured and the infusion to be carried out is planned using this patient data.

SUMMARY OF THE INVENTION

According to one aspect of the invention, there is provided a method for planning the placement of a device into a body or the movement of the device in the body. At least a part of the internal structure or the whole internal structure of the body is analyzed to determine if a critical region of the body, such as a critical anatomical structure (e.g., ventricles) or physiological or functional structure, which preferably should not be harmed, is in or near the planned trajectory of the device or within a region of interest around the planned trajectory. The device can be any device used for medical examination or treatment and, for example, can be a biopsy needle or an intra-cranial catheter. These devices should be safely introduced and placed into the body and moved therein without harming the patient. For example, the devices should not cross an optic nerve or other important anatomical or functional risk structure, while simultaneously considering the success of a medical examination or therapy by reaching a specific body structure. In other words, the devices preferably are located such that a target area is optimally provided with a substance distribution resulting from the location and trajectory of the catheter. The levels of risk resulting from a specifically planned trajectory or the difficulty in carrying out a surgical plan or medical examination associated with planned stereotactic trajectories can be assessed and related to a specific plan or trajectory of a device to be introduced into, placed in and/or moved in the body or patient. More particularly, when considering a plan for placing a device in a body, the proximity of a treatment approach, e.g., a trajectory of the device, to risk structures can be determined and the risk level of a particular treatment approach can be weighted. In this manner, for example, a plan can be drawn up such that the catheter to be placed in the body has a predetermined minimum distance from certain critical structures and, for example, stays at least a predetermined distance from critical structures (e.g., 5 mm away from sulci or 7 mm away from the optic nerve).

The three dimensional structure of the body or tissue can be considered and inaccuracies of the planning and placement approach, which may result, for example, from restricted image resolution, non-perfect patient registration, instability or flexibility of a catheter and so on, can be determined or anticipated for consideration. Then, the risk of reaching or not reaching a specific structure can be rated. For example, it can be considered that a catheter having a high flexibility may be deflected to cross a critical region, which may increase the determined level of risk. Furthermore, it can be easy to stay away from a critical area, such as a sulcus, by a predetermined distance of 5 mm at the point of entry, whereas further down the trajectory, e.g., in the body or patient, the predetermined distance of 5 mm is insufficient if an unstable catheter is used (e.g., a catheter that is likely to bend toward the risk structure).

Furthermore, inaccuracy based on the navigational approach, such as frame based or frameless, can be considered for planning the trajectory to guarantee that a specific structure is or is not reached by introducing the device. Image resolution and data accuracy can be taken into consideration to determine the accuracy of the method and thus the risk of reaching risk structures.

The risk due to a particular setup or configuration of a surgical navigation system can be considered. For delivering a probe, the holding device used in surgery bears inherent inaccuracies, e.g., if a surgeon uses a pointer to pass a catheter along a desired trajectory, the anticipated inaccuracies are higher than with a rigidly mounted holding device. Also, if the holding device is fixed far away from the entry point, the risk of inaccurate placement is elevated versus fixing the holding device close to the entry point. These inaccuracies can be determined or estimated and can be used for planning the movement of a device into or in a body or patient. A catheter having a high flexibility may be deflected into or towards a structure of risk, which would increase the respective level of risk, whereas a stiff or hard catheter may decrease this level of risk. However, in vascular structures, the stiff catheter may increase the risk of harming vascular structures compared to a more flexible catheter. Also, an experienced or a good surgeon may decrease the calculated level of risk, whereas an inexperienced surgeon may increase it.

The structures of the body or patient or a part of the body, such as the brain, can be detected automatically to detect the anatomical, functional and/or physiological structures by using, for example, known segmentation techniques. Furthermore, it is also possible to use manually outlined structures that can be identified by an experienced surgeon. These structures can be manually or automatically related to different levels of risk.

The analysis of the body or a part thereof, especially structural data, can be performed on the basis of anatomical data obtained by MRI, CT, X-Ray, ultrasound, physiological data obtained by MR-DTI, MR-DCE, perfusion imaging from MR or CT, PET, SPECT, MEG, functional data obtained by fMRI, PET, brain-mapping, EEG and/or angiographic data which enables the visualization of veins and/or arteries.

The method described herein enables automatic detection of anatomical, functional, angiographic and/or physiological structures of the body, particularly the brain and/or manually outlined structures. The structures can be identified in the internal structure of the body or in images and/or data of the internal structure of the body, and can be automatically segmented from said images. These structures can be either manually or automatically related to different levels of risk.

For example, after entering a trajectory for biopsy, catheter placement, shunt placement or stimulator placement based on the patient-specific input data and/or automatically and/or manually outlined structures, the method preferably can check for existence of critical structures in a selected area around the trajectory. The volume or region of interest can be defined as a default value or by a predetermined value around or close to the trajectory or can be defined manually by the user, or can be automatically or semi-automatically defined using information about patients and/or treatments and or the treating physicians experience. Critical regions or structures appearing within this volume can be automatically displayed and/or classified in terms of risk levels. Different risk levels can be defined in terms of proximity or likelihood of reaching this structures or can be determined based on proximity to the trajectory, anatomical characteristics, functional characteristics as well as physiological characteristics of the critical structure. Also close proximity between different trajectories can be included as a risk. In general, these characteristics can be used to assess potential risk levels for affecting functionality or any adverse effect due to the crossing of the trajectory in the respective region. Information of the identified critical structure can be displayed in terms of:

Spatial Location
Level of risk/potential adverse effect
Proximity to the trajectory Regarding spatial location, the critical area can be obtained by patient-specific image data and/or can be outlined manually by the user. In one embodiment, the segmented critical structure can be registered with an image of the part of the body and might then be overlaid on the co-registered subject image. Levels of risk can be displayed, for example, on a separate window and/or by color classification of the segmented critical structure. Warnings about the potential adverse effect from crossing this structure also can be displayed. Quantitative information regarding the proximity of the critical structure with respect to one or more trajectories can also be provided.

An application is for the use of described information for navigation systems. Virtual "walls" or boarders can be created along or around critical regions that do not allow the user or warn the user if areas behind those walls or boarders are entered.

Suggestions for trajectories that do (or do not) cross regions of predefined or predetermined risk levels can be created or determined. For example, the trajectory can be planned such that it only crosses areas or locations of a predetermined risk level but does not cross areas with a higher risk level. Furthermore, the distance from said areas which are not to be crossed by the trajectory can be related to or proportional to the height or extent of said risk level.

Information can be used for creation of suggestions for trajectories that are placed in a predefined distance to areas of predefined risk levels. This distance can be the same constant distance for every critical structure with a risk level above a predetermined risk level or can be related to or proportional to the extent of each level of risk.

The provision of haptic feedback in a delivery device, e.g., a robotic or assisting arm system, can be used, whereby the feedback may be based upon the proximity between a surgical tool moving in a known relationship to the robotic arm and regions of risk. For example, the distance of a surgical tool to critical structures can be determined repeatedly. Based on said distance and the risk level of each critical region, a strong or weak haptic feedback can be provided to make the robotic or assisting system change the direction or position of the surgical tool.

The directed delivery of electrical energy, e.g., by neurostimulation, may be based on the knowledge of the proximity of a delivery device to risk structures. Further, the directed delivery of a therapeutic agent may be based on the knowledge of the flow patterns into nearby structures of risk.

The method described herein enables the physician to focus on finding the optimal trajectory for a treatment or medical examination by providing information in terms of anatomical, functional and/or physiological information and/ or based on warnings about the potential adverse effects when chosen trajectories cross a critical area or region as outlined. Transferring the information to a surgical navigation system increases safety for the patient by excluding areas associated with high-risk levels.

In accordance with another aspect of the invention, there is provided a method for planning an infusion, e.g., for administering a substance or an active agent, in particular for injection into tissue, preferably into a predetermined tissue structure or tissue volume, wherein patient data or parameters obtained from the patient are captured. Known magnetic resonance imaging methods (MRI), computer tomography (CT) methods, x-ray methods, ultrasound methods or other suitable methods, which enable the spatial structure of a body, in particular of a tissue structure, to be detected and displayed and/or functional data, such as for example patient-specific diffusion and perfusion properties, to be obtained, can be used in this respect. Infusion can be planned as described above using the patient data (e.g., the catheter to be used is suitably selected, the catheter is positioned with respect to the insertion location and depth of penetration, the infusing medium is selected and if necessary modified, for example thinned, and the pressure gradient over time with which the infusing medium is to be delivered through the catheter is predetermined by taking into account various selectable pre-set figures, such as for example patient data or also parameters of available substances to be administered, parameters of the catheters which may be used and possibly of a pump which may be used. The aim of this selecting and setting is to inject a defined quantity of the substance to be administered into a target tissue volume, in order to obtain a particular concentration there, wherein as little of the substance to be administered as possible is to be introduced into non-target tissue.

The captured patient data may be used to position the infusion device(s), for example one or more catheters, wherein it is determined from these patient data where exactly in the patient's body a tissue volume to be treated, for example brain tumor, is situated. Using this information, a suitable catheter can be selected, for example from an available data base, by an operator or automatically, and possibly modified by post-processing, for example trimming the length of the catheter, in accordance with application or patient specifications, for example with respect to the desired depth of penetration into the tissue or the exact planned position of the catheter. Furthermore, a suitable point for inserting the catheter or how the catheter should be placed in the tissue can be determined such that the infusion debilitates as little healthy tissue and as much non-healthy tissue as possible.

Known positioning methods can advantageously be used. For example, reflecting markers that are attached to the catheter and detected by IR cameras can be used in order to locate the catheter at a desired position on the patient. To this end, markers also may be attached to the patient, wherein the markers serve as a reference and through which a patient coordinate system can be determined that enables the catheter to be placed at a particular determined point.

Patient-specific parameters preferably are determined using the captured patient data for planning the infusion, for example the tissue or body structure in the area of the tissue to be treated by the infusion. It is particularly advantageous to determine the tissue density, the distribution of particular tissue structures, or the blood flow through a particular area of tissue, as patient parameters. Patient parameters may be obtained both directly from the captured patient data as well as from databases or from a combination of values stored in databases together with the captured patient data. Thus, values which may be used as patient parameters for planning an infusion can be stored, for example values relating to usual blood flow through particular areas of tissue, the diffusion and perfusion behavior of selected substances in the tissue under consideration, and values relating to tissue behavior after a known substance has been delivered, for example swelling of the tissue or metabolic reactions.

It is furthermore advantageous to determine parameters of the infusing medium that characterize the substance to be administered or an active agent and, for example, define the physical, chemical and/or biological properties. Thus, information relating to the molecular or particle size of the substance to be administered, the rate of diffusion of this substance in a particular type of tissue, the metabolism and/or interaction of the substance with tissue due to metabolic processes, a diffusion coefficient known for the substance for the type of tissue to be treated or advantageous injection pressure or pressure gradient, an advantageous concentration, quantity or rate of delivery, whose magnitude of size is usually in the range μl/min, can be obtained from a database. The parameters of the infusing medium listed by way of example can be used individually or in combination with other parameters for planning the infusion.

Advantageously, catheter variables (i.e., variables specific to a catheter for planning the infusion) may be used, wherein various types of catheters could be provided, for example in a database, and selections may be made from these catheter types. Catheter parameters relevant to the infusion, for example, can be the inner diameter of the catheter, surface finish, the material, in particular the rigidity of the catheter, the shape, the number and arrangement of outlets on the catheter or a known suitability of a particular type of catheter for a particular substance to be administered or a particular type of tissue or diseased tissue to be treated. In general, a number of catheters may also be used.

A physiological fluid, a pharmaceutical substance, a solution containing cells, viruses, viral vectors, genes, enzymes, proteins, liposomes, hormones, antibodies or a combination of those can be used as the infusing medium.

By using the patient parameters, parameters of the infusing medium and/or catheter parameters cited above by way of example, individually or in combination, together with the captured patient data, an infusion to be performed can be planned, such that as large a proportion of a substance as possible is introduced into a target area of tissue by infusion, wherein as little of the substance as possible is released into non-target tissue. Thus, a substance to be introduced into a tissue by infusion can be introduced into an area of tissue to be treated in the patient using a particularly suitable and correctly positioned type of catheter and the correct injection pressure, at a suitable concentration and at a desired rate, taking into account metabolic and convective and/or diffusive and/or perfusive processes, in order to obtain a desired concentration of the substance to be introduced in said area of tissue, wherein, for example in the case of brain tumors, the effect of the blood-brain barrier may be bypassed by directly injecting the substance by infusion. Surrounding tissue is thus debilitated as little as possible.

In order to pre-plan the infusion, a simulation of the infusion to be performed can advantageously be calculated, for example by calculating the distribution of infusing medium in the tissue using the captured patient data and the various parameters mentioned above. Using such a simulation, the distribution of the infused medium can be determined both statically and dynamically as a function of time, and advantageously graphically displayed. In this way, it can be established even before performing an infusion whether a desired concentration distribution of the substance to be introduced in the target tissue can be obtained, or whether parameters of the infusing medium, catheter parameters or position parameters possibly have to be altered, to ensure a more successful infusion.

Furthermore, retro or inverse planning also can be performed, wherein for example treatment data defined by an operator may be pre-set, such as for example the target volume to be treated, advantageously together with high-risk structures such as for example nerve tracts that should not be compromised by the infusion, levels of risk of regions of the tissue, and details of the type of tissue to be treated. In this way, either automatically or by interaction with the operator, for example by displaying a selection menu, the course of the infusion can be established (e.g., one or more types of catheters can be selected together with suitable infusing media, the arrangement(s) of catheters can be determined with respect to position and/or depth of penetration and the parameters of the infusing medium can be set) in order to enable a optimal infusion treatment for the given target volume.

The planning methods described above, in particular the selecting of individual parameters and the segmentation of critical regions of the tissue and the determination of levels of risk in said region, can be performed: fully automatically using, for example, values stored in data bases; semi-automatically, for example by selections made by an operator from a displayed menu; or manually, for example through parameter values input by an operator. In this respect, suitable computers can be advantageously used, together with input and output elements, for example display elements displaying elements to be selected, tissue structures, calculated concentration distributions of the infusing medium and other information.

In accordance with another aspect of the invention, there is provided a computer program which, when loaded or running on a computer, performs the method described above or parts of it. Equally, the present invention relates to a storage medium for such a program or to a computer program product comprising the aforementioned program.

A device for planning an infusion, comprises a planning system including a computer system, preferably having input and output devices and corresponding software. In this respect, a monitor can be advantageously provided for displaying elements pre-set by the computer from databases or values determined from calculations or spatial distributions.

A navigation system can be provided, including, for example, reflecting markers, LEDs or coils attached to elements to be positioned and IR cameras or magnetic field generators, with which a catheter on a body, for example, can be positioned using a suitable, known software and hardware.

Generally, the device can include elements, devices and systems with which the steps of the method described above may be performed.

In accordance with another aspect of the invention, there is provided an infusion method, wherein infusion is preferably prepared as described above and the infusing medium is then introduced into the body or tissue.

Verification can be performed continuously or at particular intervals in time during the infusion. The distribution of the infusing medium in the tissue during or after the infusion process can be determined using a suitable data capture or representation system. Magnetic resonance imaging, x-ray based methods, or ultrasound methods, for example, may be used in this respect, wherein it may be advantageous to add a contrast medium to the infusing medium in order to clearly establish or measure the distribution of the infusing medium in the body tissue.

Preferably, deviations between the actual distribution of the infusing medium in the tissue and the planning data (which may be determined before or during the infusion) as determined from the verification process can be displayed. Advantageously, the infusion parameters may be corrected, e.g., the chemical and/or physical composition and/or properties of the infusing medium may be changed and/or the delivery may be changed, for example the injection pressure or quantity delivered may be changed to be able to correct for the deviation, determined during verification, from the planned distribution. If necessary, a catheter also can be repositioned or exchanged.

Advantageously, the deviation can be determined, verified and the correction made in real time, such that the infusion can be controlled via a back-coupling (e.g., feedback) to obtain the desired successful infusion, i.e., to deliver the infusing medium to the given target area as desired.

In accordance with a further aspect of the invention, there is provided a computer program which, when loaded or when running on a computer, performs the method described above. Equally, the present invention relates to a storage medium for such a program or to a computer program product comprising the aforementioned program.

According to a further aspect of the invention, there is provided a device for carrying out an infusion method as described above, comprising a verification device for determining the spatial distribution of an infusing medium in a body, in particular in an area of tissue. The verification device, for example, can be a magnetic resonance or nuclear spin resonance, x-ray, or ultrasound system with which the infusing medium or its distribution and concentration in the tissue can be detected.

A computer system can be provided with a display device to enable evaluation of the determined spatial distribution of the infusing medium in the tissue, to establish a deviation from a previously established infusion plan and possibly to automatically alter the infusion parameters or propose such a change to an operator, in order to modify the infusion such that it can be carried out as planned. To this end, systems can be provided that enable the concentration of the infusing medium to be changed and/or the injection pressure or injection quantity can be altered by means of a pump, to obtain a distribution of the infusing medium in the tissue as previously planned. When a deviation from a given infusion plan is established during verification, the manner and magnitude of the change to the infusion parameters can be advantageously determined using known action and function mechanisms. For example, the rate of delivery or the injection pressure can be reduced when it is established that the infusing medium is spreading faster than predicted or is not being degraded by metabolic processes as quickly as expected.

BRIEF DESCRIPTION OF THE DRAWINGS

The forgoing and other features of the invention are hereinafter discussed with reference to the drawings.

DETAILED DESCRIPTION

Figure 1A:
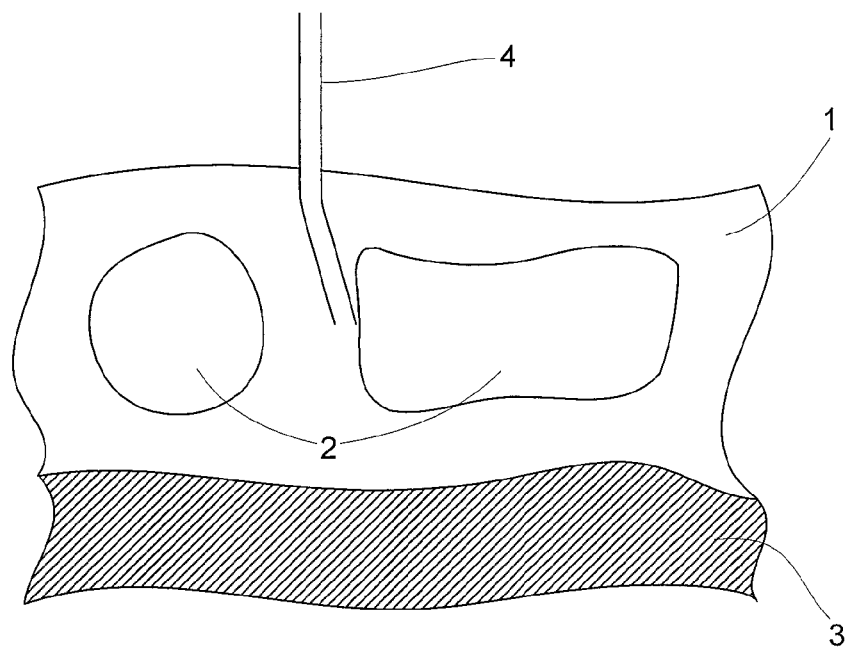
FIGS. 1a and 1b are exemplary images acquired and displayed in accordance with a method of the present application.

FIG. 1a shows an image acquired using an exemplary method for planning the movement and placement of a catheter 4 in tissue 1 of a patient. The patient 1 has structures of risk 2, e.g., damageable regions, and a target region 3, e.g. a region to be treated, such as a tumor. For efficiently treating the tumor 3, it is desirable to position the catheter 4 as near as possible to the tumor 3 or directly into the tumor 3 so that the treatment substance can be directly injected into the tumor. The remainder of the tissue should not come into contact with the substance. Further, the catheter 4 should not cross the structures of risks 2 and should not be placed in close proximity to the structures of risk 2. For this purpose, an ultrasound imaging system can be used to image and display the tissue 1, as shown in FIG. 1a, so that the movement and placement of the catheter 4 can be planned and controlled. As shown in FIG. 1a, a catheter 4 is inserted into the tissue 1 at a position suspected or determined to be the best position for treating the tumor 3 without harming or damaging the structures of risk 2. However, as shown in FIG. 1a, due to the internal structure of the tissue or due to the properties of the catheter 4, the catheter bends toward the structure of risk 2.

Further to displaying the tissue 1 and the movement of the catheter, a warning device outputs a warning signal when the catheter 4 comes within a predetermined distance of the structure of risk 2 (e.g., a safety range around the structure of risk 2). When the catheter crosses this safety range, the warning device outputs a warning signal, e.g., an audible signal or an image indicating danger, such as a yellow bar or a yellow sign. If the warning signal is ignored by the surgeon and the catheter 4 comes even closer to the structure of risk 2, the warning signal may be increased, e.g., the volume of the signal may be increased, or the color of the image may be changed, such as a red bar or a red sign. Considering this warning signal, the catheter movement can be corrected or the catheter 4 can be pulled out of the tissue 1.

Figure 1B:
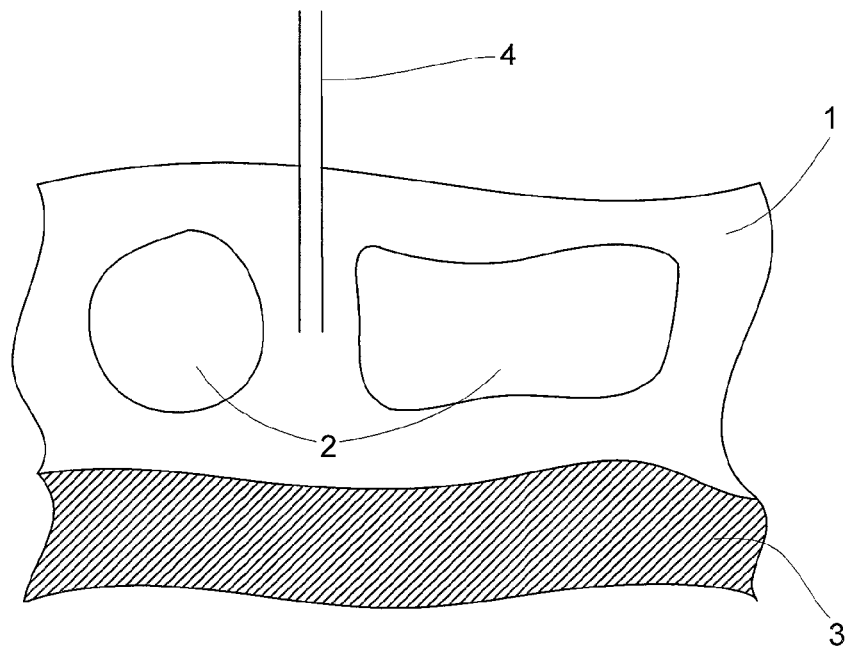

FIG. 1b shows another attempt of positioning and moving the catheter 4 such that the catheter 4 is directly inserted into the tumor 3 and the tumor can be ideally treated. By changing conditions or considering certain conditions, such as changing the entry point of the catheter 4, or using a different catheter 4 such as a more compact catheter, or by considering the internal structure of the tissue 1 so as to determine a different trajectory or a different pathway to the tumor 3, the catheter 4 does not come close to the structures of risk 2 and does not cross the safety region around the structures of risk 2. As a result, no warning signal is output by the warning device and the catheter can be perfectly inserted into the tumor 3.

Figure 2:
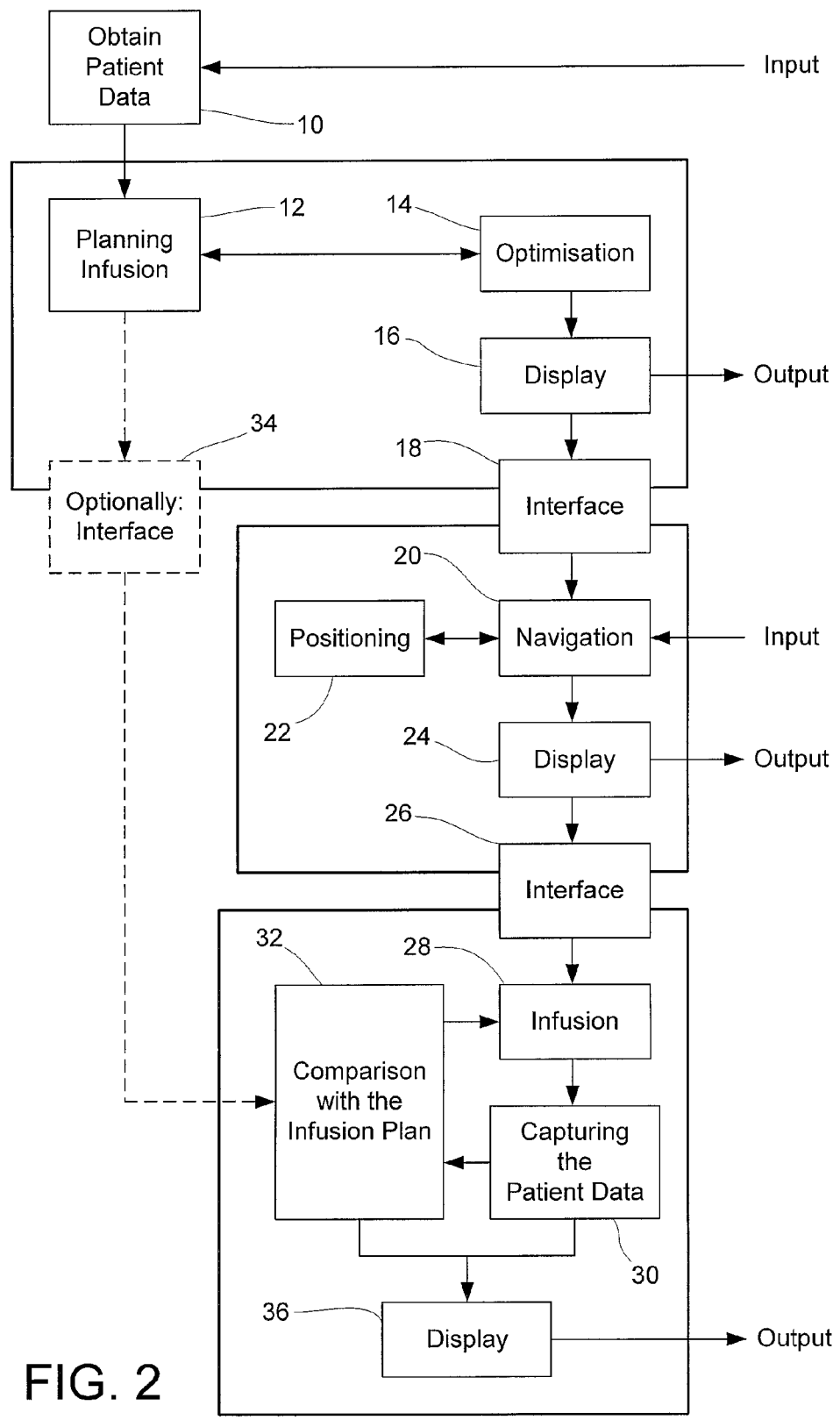
FIG. 2 is a schematic diagram of an exemplary method for planning and carrying out an infusion.

FIG. 2 shows a schematic flow diagram for preparing and carrying out an exemplary infusion. As shown in FIG. 2, at block 10 patient data are input, for example from a magnetic resonance or nuclear spin tomograph. The data may be used to determine a particular target area of tissue for the infusion and to plan the infusion dosage to be delivered. The data can be obtained, for example, through the magnetic resonance or nuclear spin resonance system 60 as shown schematically in FIG. 4 after the patient has been examined. Using parameters for the properties of the tissue structures, such as data of levels of risk of critical structures, and for various types of catheters stored, for example, in databases, and once the exact location of the tissue volume to be treated has been determined, then one or more catheters suitable for the infusion can be selected. At block 12, the patient parameters obtained, for example by the magnetic resonance or nuclear spin resonance method, can be used together with the catheter parameters and the parameters of the infusing medium, also for example stored in databases, to plan the infusion. At block 14, the corresponding parameters can be optimized on the ancillary condition that a large as possible proportion of the infusing medium is introduced into the target tissue at the desired concentration, wherein as little of the infusing medium as possible is to reach tissue lying outside the target tissue. In general, as few catheters or needles as possible should be placed, said catheters or needles being fed through as few access ports as possible. At block 16, this optimized planning of the infusion dosage can be output via a display. For example, a two-dimensional or three-dimensional representation can be output through representations of various incision planes, in order to display the results of infusion plan.

Figure 4:
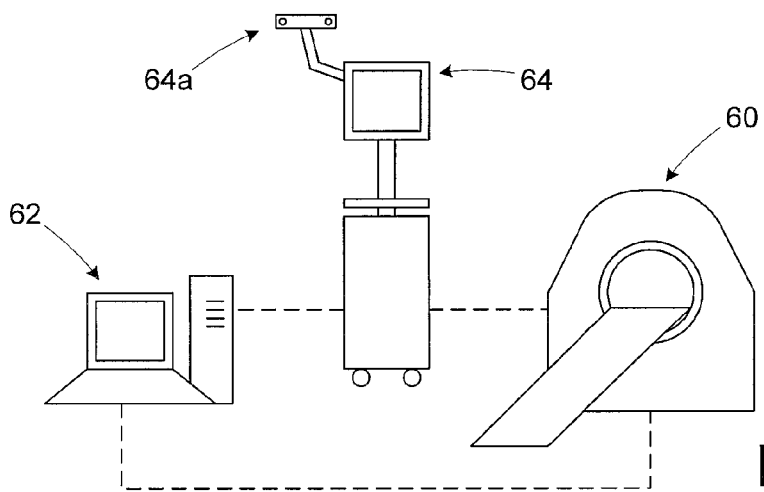
FIG. 4 is a device that may be used when planning and carrying out an infusion in accordance with the invention.

At blocks 18 and 20, the infusion plan can be communicated via an interface to a navigation system, such as for example the VectorVision® system shown schematically in FIG. 4. At block 22, the navigation system can be used to position the selected catheter or catheters at the given points on the body based on the planning data. The catheter(s) can be positioned automatically, for example using a robot, or manually with guidance from the navigation system (e.g., a display device showing whether the catheter is correctly positioned or still has to be moved in a particular direction). At block 24, the results of the positioning and navigation may be output to a display device.

Once the catheter(s) has/have been successfully positioned, then at block 26, data may be communicated to an infusion device (e.g., the infusion parameters may be transferred to the infusion device and a command may be provided to instruct the infusion device to commence with the infusion) and at block 28 the actual infusion can be carried out using the parameters of the infusing medium set by the planning. To this end, patient data are captured at block 30 to determine the actual distribution of infusing medium in the tissue. Using the parameters set during planning, and the results of the simulation of the infusion based on the plan, at block 32 a comparison can be made between the actual distribution of the infusing medium and the predicted, desired distribution of the infusing medium. At block 34, the comparison data can be communicated back to block 12, wherein the parameters (e.g., the concentration of injected medium, the quantity delivered or the injection pressure for carrying out the infusion) can be altered as appropriate, preferably taking into account known action mechanisms in order to obtain the desired, planned infusion result. The measured, actual distribution of the infusing medium concentration, preferably together with possible deviations and correcting methods, can again be output via a display at block 36 to enable an operator, for example, to manually intercede in the injection method.

Figure 3:
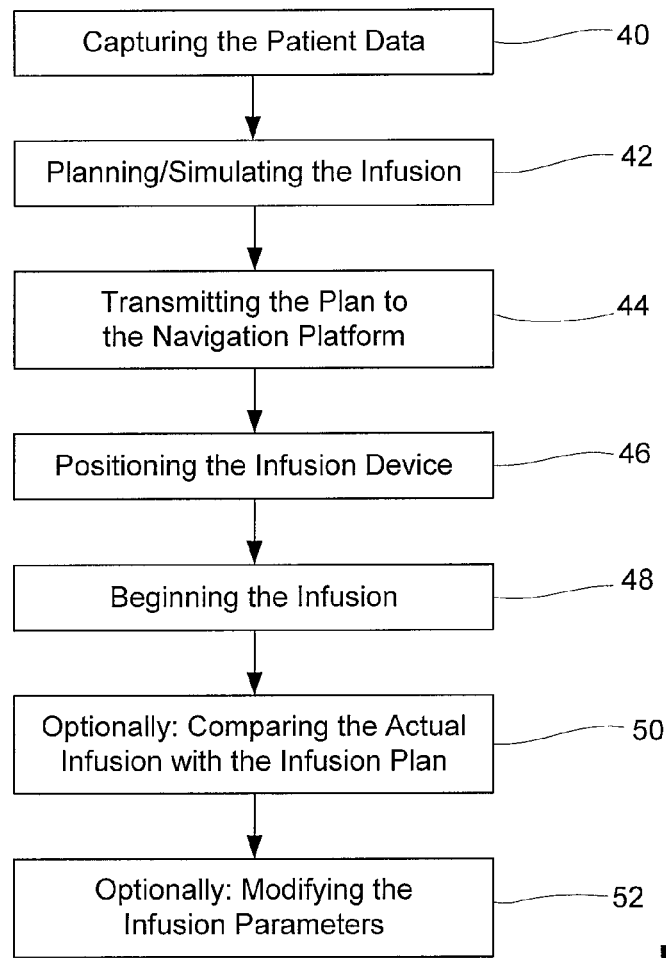
FIG. 3 is a simplified flow diagram of an exemplary infusion performed in accordance with the invention.

FIG. 3 schematically shows a simplified exemplary sequence of planning and carrying out an injection. At block 40, patient data are captured using an imaging diagnostic method such as, for example, a magnetic resonance or nuclear spin resonance method, to obtain the current patient parameters (e.g., tissue density, blood flow, and the location of a tissue to be treated). Using the patient parameters determined in this way (e.g., data of levels of risk of critical regions) and with catheter parameters and parameters of the infusing medium obtained from a database and/or pre-set for a particular infusion, the infusion can be planned and/or simulated at block 42. Based on the parameter data determined in this way, at block 44 the infusion plan is forwarded to a navigation platform, which at block 46 can be used to position the catheter or catheters on the patient as provided for in the infusion plan. At block 48, infusion begins once the infusion device has been positioned and is carried out using the planned and possibly simulated parameters. At block 50, the actual infusion data is optionally compared with the planned infusion data, and in the event of deviations, the corresponding parameters are modified, preferably using known action mechanisms, as indicated at block 52.

FIG. 4 schematically shows a system that may be used when planning and carrying out an infusion in accordance with the invention. Patient data are obtained in a magnetic resonance or nuclear spin tomograph 60 and forwarded to a planning system 62 and to a navigation system 64. The catheter or catheters may be positioned at a desired point on a body by the navigation system 64 using, for example, known reflectors or markers attached to one or more catheters, positional data of the markers being captured by IR cameras 64*a*. In order to carry out the infusion, the planning system 62 determines the suitable catheter parameters and parameters of the infusing medium for a pre-set infusion to be carried out, using patient parameters determined by the magnetic resonance or nuclear spin resonance system 60.

Figure 5:
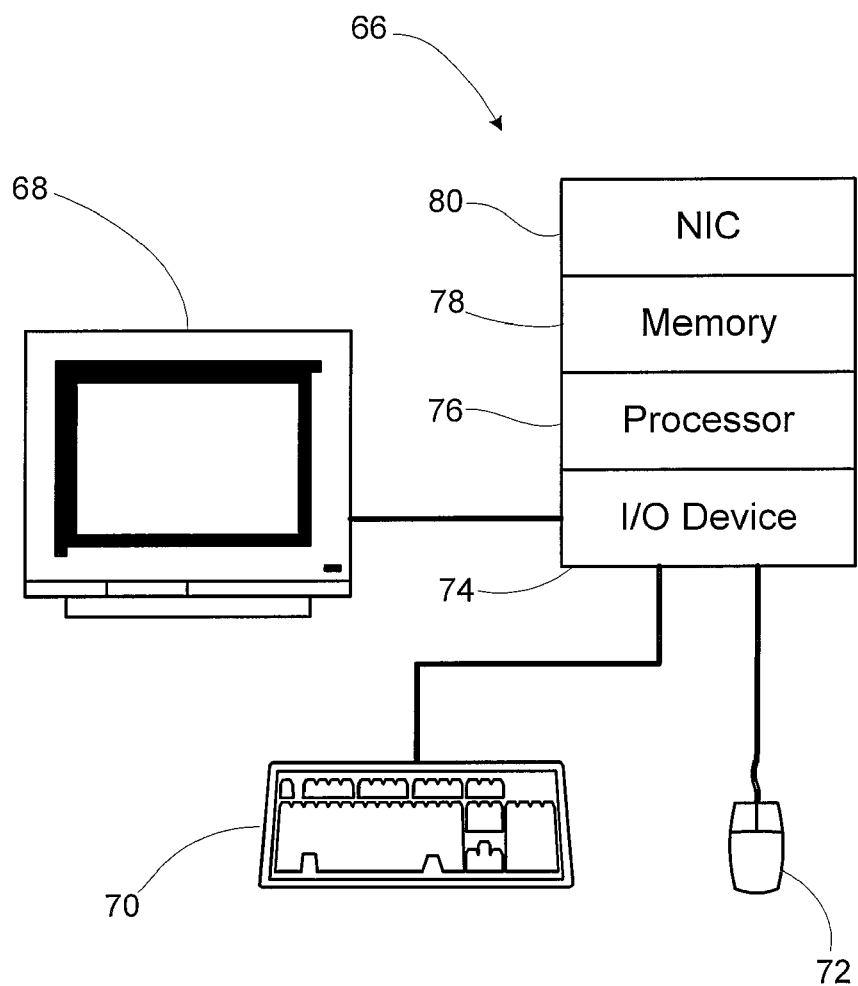
FIG. 5 is a block diagram of an exemplary computer system that can be used to carry out the method in accordance with invention.

FIG. 5 illustrates the exemplary computer system 66 that may be used to implement the method described herein (e.g., as a computer of the planning system 62). The computer system 66 may include a display 68 for viewing system information, and a keyboard 70 and pointing device 72 for data entry, screen navigation, etc. A computer mouse or other device that points to or otherwise identifies a location, action, etc., e.g., by a point and click method or some other method, are examples of a pointing device 72. Alternatively, a touch screen (not shown) may be used in place of the keyboard 70 and pointing device 72. The display 68, keyboard 70 and mouse 72 communicate with a processor via an input/output device 74, such as a video card and/or serial port (e.g., a USB port or the like).

A processor 76, such as an AMD Athlon 64® processor or an Intel Pentium IV® processor, combined with a memory 78 execute programs to perform various functions, such as data entry, numerical calculations, screen display, system setup, etc. The memory 78 may comprise several devices, including volatile and non-volatile memory components. Accordingly, the memory 78 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 76 and the memory 78 are coupled together via a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 80 allows the computer system 66 to communicate with other devices.

A person having ordinary skill in the art of computer programming and applications of programming for computer systems would be able in view of the description provided herein to program a computer system 66 to operate and to carry out the functions described herein. Accordingly, details as to the specific programming code have been omitted for the sake of brevity. Also, while software in the memory 78 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for planning the placement of a device in a body of a patient, comprising:

analyzing information of at least part of an internal structure of the body of the patient to determine if at least one specific or critical region or structure lies within a region of interest, said region of interest within a predetermined distance of a planned trajectory of the device in the body;

using a processor to assess a level of risk to the at least one specific or critical region or structure that is within the region of interest, wherein levels of risk are determined based on risk due to at least one of patient-specific diffusion and perfusion properties or physiological characteristics of the specific region or structure of the body, and wherein the levels of risk are determined based on at least one of:

a) risk due to anatomical, functional and/or physiological characteristics of the specific region or structure of the body, including
  i) risk of harming the body including the risk of crossing the trajectory of the device in the body with an optical nerve, and/or
  ii) risk of unsuccessful treatment including the risk of crossing the trajectory of the device in the body through a Sulcus in drug delivery;
b) risk due to a predefined treatment plan, said risk due to the predefined treatment plan including a proximity of a treatment approach or trajectory to a risk structure, the proximity of two or more different treatment approaches or trajectories to each other, and/or weighting the risk of the predefined treatment approach; or
c) risk due to a predefined setup or configuration of a surgical navigation system;

and displaying borders along or around the specific or critical region or structure, wherein when planning the trajectory to cross at least one border, a warning signal is output or the trajectory is prevented from crossing the border.

2. The method according to claim 1, wherein analyzing information includes automatically detecting the information of the at least part of the internal structure of the body, wherein said information includes at least one of anatomical, functional, angiographical and/or physiological structures of the body.

3. The method of claim 2, wherein automatically detecting includes automatically detecting structures that are manually outlined.

4. The method according to claim 2, wherein the anatomical structures are obtained using at least one of Magnetic Resonance Imaging (MRI), X-Ray Imaging, Computer Tomography (CT) Imaging, or Ultra Sound Imaging, the physiological structures are determined using at least one of MR-DTI, MR-DCE, perfusion imaging from MR or CT, PET, SPECT, or MEG, and the functional structures are determined using at least one of fMRI, PET, brain-mapping, or EEG.

5. The method according to claim 1, further comprising automatically displaying, classifying and/or assessing in terms of levels of risk, spatial location, potential adverse effect and/or proximity to the trajectory, the specific or critical region or structure in the region of interest.

6. The method according to claim 1, further comprising defining the region of interest around the trajectory based on a user entry, or automatically or semi-automatically defining the region of interest based on patient information.

7. The method according to claim 1, further comprising identifying in the information of at least a part of the internal structure of the body the specific or critical region or structure, and segmenting the specific or critical region or structure from the information of the internal structure of the body.

8. The method according to claim 7, further comprising registering the segmented specific or critical region or structure with an image of the part of the internal structure of the body and overlaying segmented specific or critical region or structure with the image.

9. The method according to claim 1, further comprising using at least one of MRI diffusion scans, MRI-contrast enhanced scans, DTI, MRI dynamic contrast enhanced scans, CT perfusion scans, MRI T1w scans, MRI T2w scans, MRI proton density scans, MRI spectroscopy scans, PET scans, SPECT scans, molecular imaging, CT, X-ray, ultrasound, elastography, time series imaging, biopsies and/or tissue analysis to obtain the specific or critical region or structure.

10. The method according to claim 1, further comprising displaying the specific or critical region or structure together with the planned trajectory on the image of the internal structure of the body.

11. The method according to claim 1, wherein weighting the risk of the predefined treatment approach includes weighting the risk of a catheter plan or trajectory that is at least a predetermined distance away from a sulcus.

12. The method according to claim 1, wherein the risk due to a predefined setup or configuration of the surgical navigation system includes the risk associated with using an unmounted holding device, the risk associated with using a flexible infusion or holding device, the risk associated with the holding device being fixed or mounted greater than a predetermined distance from an entry point of the catheter, and/or the risk associated with an inexperienced surgeon.

13. The method according to claim 1, further comprising separately displaying levels of risk and/or displaying the levels of risk in the specific or critical region or structure.

14. The method according to claim 1, further comprising determining trajectories that do or do not cross regions of a predetermined level of risk.

15. The method according to claim 1, further comprising providing haptic feedback to a guiding device, whereby the haptic feedback is based upon a proximity between a surgical tool moving in a known relationship to the patient and regions of risk.

16. The method according to claim 1, further comprising providing a warning about a potential adverse effect of the planned placement of the device.

17. The method according to claim 1, further comprising providing quantitative information regarding the proximity of the specific or critical region or structure with respect to one or more trajectories.

18. The method according to claim 17, wherein the warning is an audible warning or a visual warning.

19. The method according to claim 1, further comprising using the planned trajectory for at least one of stereotactic biopsies, catheter placement, cannula placement, stimulator placement, shunt placement, or surgical implant placement.

20. The method according to claim 1, further comprising delivering electric energy to a region or structure based on a proximity of the delivery device to the specific or critical region or structure.

21. The method according to claim 1, further comprising delivering a therapeutic agent to a region or structure based on the information of flow patterns into nearby specific or critical regions or structures.

22. A method for planning the placement of a catheter in a body of a patient, said catheter having a specific rigidity chosen from various types of catheters stored in a database, comprising:

analyzing information of at least part of the internal structure of the body of the patient to determine if at least one specific or critical region or structure lies within a region of interest, said region of interest within a predetermined distance of a planned trajectory of the catheter in the body;

using a processor to assess a level of risk to the at least one specific or critical region or structure that is within the region of interest, wherein the level of risk and the rigidity of the catheter are determined based on risk due to patient-specific tissue density of a specific region or structure of the body and wherein the levels of risk are determined based on at least one of:

a) risk due to anatomical, functional and/or physiological characteristics of the specific region or structure of the body, including i) risk of harming the body including the risk of crossing the trajectory of the device in the body with an optical nerve, and/or ii) risk of unsuccessful treatment including the risk of crossing the trajectory of the device in the body through a Sulcus in drug delivery;

b) risk due to a predefined treatment plan, said risk due to the predefined treatment plan including a proximity of a treatment approach or trajectory to a risk structure, the proximity of two or more different treatment approaches or trajectories to each other, and/or weighting the risk of the predefined treatment approach; or c) risk due to a predefined setup or configuration of a surgical navigation system; and displaying borders along or around the specific or critical region or structure, wherein when planning the trajectory to cross at least one border, a warning signal is output or the trajectory is prevented from crossing the border.

* * * * *